United States Patent [19]

Lau et al.

[11] Patent Number: 4,940,812
[45] Date of Patent: Jul. 10, 1990

[54] 5-SUBSTITUTED AMINOPHENOLS

[75] Inventors: Philip T. S. Lau, Rochester; Danny R. Thompson, Fairport, both of N.Y.

[73] Assignee: Eastman Kodak Company, Rochester, N.Y.

[21] Appl. No.: 380,347

[22] Filed: Jul. 17, 1989

[51] Int. Cl.$^5$ ............................................. C07C 147/13
[52] U.S. Cl. ........................................ 560/12; 560/13; 560/15; 562/426; 562/430; 564/440; 548/251; 548/260; 548/261; 548/311; 558/13; 558/179; 558/184
[58] Field of Search .................... 562/426, 430, 457; 560/12, 13, 15

[56] References Cited

U.S. PATENT DOCUMENTS

| | | | |
|---|---|---|---|
| 3,637,803 | 1/1972 | Shen et al. | 562/430 |
| 3,779,763 | 12/1973 | Lau | 430/432 |
| 4,242,519 | 12/1980 | Tsuchihashi et al. | 560/15 |
| 4,741,846 | 5/1988 | Evans | 560/9 |

FOREIGN PATENT DOCUMENTS 46-00020 1/1971 Japan .................................. 562/426

OTHER PUBLICATIONS

Philip T. S. Lau et al., J. Org. Chem., 28, 2763, (1963).

*Primary Examiner*—Glennon H. Hollrah
*Attorney, Agent, or Firm*—Robert A. Linn

[57] ABSTRACT

Process for the introduction of functional or functionalizable substituents para to the amino group in 2-aminophenols and 3-aminophenols. The process proceeds in one step, with substitution occurring selectively at the position para to the amino group. Consequently, the reaction is surprisingly straightforward, with very little or no contamination by isomeric by-products. The process comprises reaction of (a) an aminophenol having an open para position to the amino function, with (b) an unhindered non-enolizble aldehyde, and (c) a thiol or sulfinic acid which acts as a nucleophile. In preferred embodiments, the process is conducted at a temperature of from about 50° C. to about 100° C., and in the presence of a polar solvent. The reaction is promoted by an acid having sufficient acidity to protonate the amino group of the aminophenol. Preferably, the acid promoter is a mineral acid, and it is present in an amount at least substantially equivalent to the amount of aminophenol reactant. The promoter can be added as a salt of the aminophenol.

4 Claims, No Drawings

5-SUBSTITUTED AMINOPHENOLS

FIELD OF THE INVENTION

This invention relates to aminophenols having substituents para to the amino function, and to a process for their formation. More particularly, this invention relates to 2-aminophenols and 3-aminophenols which have a functional or functionalizable substituent at the position para to the amino group. These materials are useful as chemical intermediates, e.g., for the preparation of color photographic dye formers.

The compounds of this invention are prepared by a process which comprises reacting (a) an aminophenol with (b) an unhindered non-enolizable aldehyde and (c) a thiol or a sulfinic acid, in the presence of an acid promoter. Unlike most electrophilic substitution reactions of activated aromatic compounds, which lead to a mixture of isomeric substituted products, the reaction of our invention is surprisingly clean, with essentially one product being formed. In other words, substitution occurs selectively in the position para to the amino group. Thus, the product has little or no contamination caused by formation of isomeric by-products. The process comprises a reaction in which substitution can be considered to be directed and controlled by the amino group, with little or no directing influence from the powerfully activating hydroxy group in the aminophenol. The process is highly significant because it comprises a one step synthesis to the production of compounds having useful substituent groups para to the amino group.

BACKGROUND OF THE INVENTION

It is known in the art that both the amino and the hydroxy group are ortho and para directing. It is also known that when both groups are on an aryl ring, substitution reactions generally lead to a mixture of ortho and para isomers, and frequently to polysubstituted products. Needless to say, the formation and separation of isomeric mixtures greatly reduces product yields. For example, the synthesis of 2-amino-5-methylphenol involves only two reaction steps: (1) nitration of 3-methylphenol (meta-cresol) and (2) reduction of the nitro intermediate. However, the overall yield is very poor (less than 30%), due to the formation of other nitro isomers and the need to separate this mixture by steam distillation.

It is known in the art that 5-substituted-2-aminophenols are useful intermediates, for example, in the photographic industry. Unfortunately, this type of compound is generally hard to make in pure form and in good yield, for the reasons stated above.

As stated more fully below, one co-applicant herein has already provided a facile method for making a type of 5-substituted-2-aminophenols, and in a prior patent disclosed that the compounds are useful in the photographic arts. Although the compounds and process of this invention can be considered to be analogous to such prior compounds and processes, the present invention is unique from several viewpoints. First, it comprises a method for producing a desired compound substantially free from unwanted isomeric by-products. Second, the products of this invention car be produced in high yield, e.g., greater than 85%. Third, it provides a one-step introduction of a functional carboxy group or an aromatic ring containing functional or functionalizable groups into the 2-aminophenols or 3-aminophenols. To introduce these same substituents by established methods would require multistep reaction sequences and tedious separation of the resulting isomeric mixtures.

The problems faced by the Applicants were twofold. The first problem was the provision of a method for preparing derivatives of 2-aminophenols and 3-aminophenols in which a substituent group is directed to the position para to the amino group. As pointed out above, this is a difficult problem because of the presence of the powerfully directing hydroxy group bonded to the aromatic nucleus. The second problem was the provision of new compounds in which the para substituent has functionality which makes it possible to undergo further chemical reaction with other species to form new compounds. This part of the problem was also formidable because of the lack of precedence in the art. The task became even more difficult when, during the course of Applicants' investigations, it was demonstrated that seemingly related reactants failed to react, or yielded an entirely different product.

Applicants' invention solves both problems mentioned above. Furthermore, it provides a simple, one-step synthesis to compounds not previously known, and which are useful for preparing other chemicals of significant interest in the photographic and other arts. Thus, this invention is considered to be a significant advance in synthetic organic chemistry.

Related Art

The following references disclose that 2-amino-5-methylphenol is produced in poor yield when meta-cresol is nitrated and then reduced:

R. C. Huston et al, *J. Am. Chem. Soc.* 55, 3879 (1933)

W. Staedal et al, *Ann. Chem.* 259, 210 (1890)

J. Arient, *Collect Czech. Chem. Comm.* 45, 3164 (1980)

The following reference discloses reaction of aromatic thiols, formaldehyde, and aromatic amines to produce N-arylaminomethyl aryl sulfides:

Philip T. S. Lau et al, *J. Org. Chem.* 28, 2763 (1963).

U.S. Pat. No. 3,779,763 discloses 5-aryl thiomethyl-2-amino-phenols, 5-aryl sulfonylmethyl-2-aminophenols, and 5-aryl selenomethyl-2-aminophenols having utility as color photographic couplers. Also disclosed is a process for producing the couplers by reacting (a) a 2-aminophenol with (b) formaldehyde and (c) an arylthiol, arylsulfinic acid, or an arylselenol.

SUMMARY OF THE INVENTION

This invention provides aminophenols having a functional or functionalizable group in the position para to the amino group. Thus, this invention provides 5-substituted-2-aminophenols, and 6-substituted-3-aminophenols. These compounds can be considered to be aminophenol derivatives in which there are two groups bonded to the methyl carbon atom appended to the ring. One of these groups is sulfur-containing. The other is a functional or functionalizable group conferred by the non-enolizable aldehyde used as a reactant in the process of this invention.

Besides providing new chemical compounds, this invention provides:

A one-step process for the preparation of an aminophenol with a functional or functionalizable substituent para to the amino group, said process comprising reacting (a) an aminophenol having no substituent other than hydrogen para to said amino group, with (b) a non-enolizable aldehyde, and (c) a reactant selected from the class consisting of arylthiols and sulfinic acids; said process being conducted in the presence of an acid promoter.

As discussed above, this process provides a means to introduce in one simple step, functional or functionalizable groups which ca:: be used for further chemical transformations. Thus, for example, this invention provides a substituent (para to the amino group in the aminophenol) which contains a carboxy radical, —COOH. Because it is readily reacted with other materials, the carboxy radical is considered a functional group. As another example, this invention provides a para substituent which contains a group depicted by:

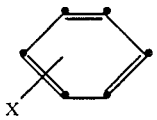

wherein X is functional, (e.g., —COOH or —OH) or "functionalizable." Thus, X in the above formula can be the "functionalizable" group —NO$_2$. The nitro radical can be transformed to the functional group —NH$_2$ by a reduction step. Thus, for the purpose of this invention the term "functionalizable" means a chemical moiety which is comparatively non-reactive, but which can be transformed to a "functional" moiety by one or more chemical reactions.

The compounds of this invention can be used as reducing agents, antioxidants, and as intermediates for the preparation of antioxidants and dyes. Dyes prepared from the compounds of this invention can be used in the photographic arts. Other dyes can be for use in the non photographic arts.

DESCRIPTION OF PREFERRED EMBODIMENTS

This invention provides as new compositions of matter compounds having one of the following formulae:

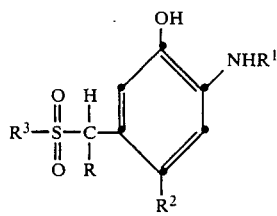
(A)

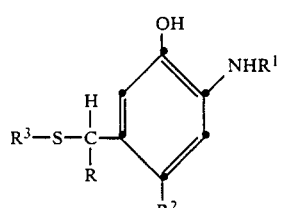
(B)

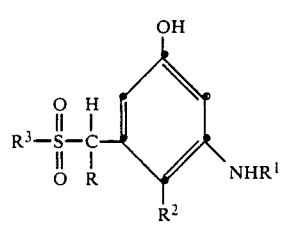
(C)

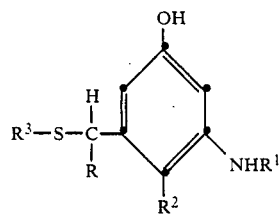
(D)

In the formulae (A) through (D), (a) R is a functional or functionalizable group selected from the class consisting of:
  (i) —COOR$^4$, wherein R$^4$ is hydrogen or a substituted or unsubstituted alkyl or aryl radical having up to about 30 carbon atoms; and (ii) 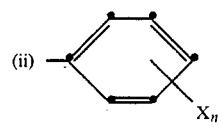

(ii) equal to zero or to a small whole number equal to or less than 5, and X is —COOR$^4$, —NO$_2$, —OH, or a substituted or unsubstituted alkyl or aryl radical having up to about 30 carbon atoms, (b) R$^1$ is selected from the class consisting of hydrogen, and substituted or unsubstituted alkyl or aryl groups having up to about 30 carbon atoms, (c) R$^2$ is hydrogen or a coupling off group, and (d) R$^3$ is a substituted or unsubstituted alkyl or aryl group having up to about 30 carbon atoms.

Thus, it can be seen that this invention provides an aminophenol wherein the amino group and the hydroxy group are either ortho or meta to one another, and wherein the amino group has at least one hydrogen bonded to the amino nitrogen, and the third valence of said nitrogen is satisfied by bonding to hydrogen or a substituted or unsubstituted alkyl or aryl group having up to about 30 carbon atoms. In these compounds the position para to said hydroxy group is unsubstituted, or substituted with a coupling off group such as F, Cl, alkoxy, or aryloxy. Also, the position para to the amino group is bonded to a carbon atom that is in turn bonded to (i) a hydrogen atom, (ii) a substituent selected from the class consisting of alkylthio, arylthio, alkylsulfonyl, and arylsulfonyl groups wherein the alkyl and aryl groups are substituted or unsubstituted and have up to about 30 carbon atoms, and (iii) a group selected from carboxy, (—COOH), carboxy ester

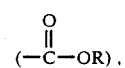

and aromatic radicals. In the carboxy ester radicals R is a substituted or unsubstituted alkyl or aryl radical having up to about 30 carbon atoms. Said aromatic radical is substituted or unsubstituted, and may have up to about 30 carbon atoms.

Preferred compounds of the above type are 5-arylthiomethyl-2-aminophenols, 5-arylsulfonylmethyl-2-aminophenols, 6-arylthiomethyl-3-aminophenols, and 6-arylsulfonylmethyl-3-aminophenols wherein as pointed out above, the methyl group attached to the aminophenol ring is substituted with a functional or functionalizable group selected from carboxy, carboxy ester, or aryl. This additional substitution on the methyl group is a highly significant feature. Compounds having such substituents were heretofore unknown. Furthermore, this additional substitution provides means for making other new compounds having many utilities such as those mentioned above.

Of these compounds, a preferred type is a 5-substituted-2-aminophenol represented by the formula:

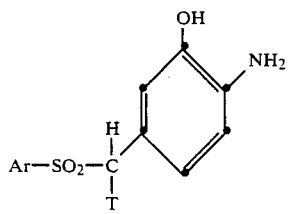

wherein Ar is a substituted or unsubstituted aryl group having up to about 30 carbon atoms, and T is a carboxy or carboxy ester group of about 30 carbon atoms, or a substituted or unsubstituted aryl group having up to about 30 carbon atoms.

The analogous 6-substituted aminophenols comprise another preferred class of compounds of this invention.

The analogous 5-substituted-2-aminophenols and 5-substituted-3-aminophenols in which the —SO₂—linking group is replaced by —S— also comprise preferred classes of compounds of this invention.

Another type of preferred compound comprises the compounds illustrated by:

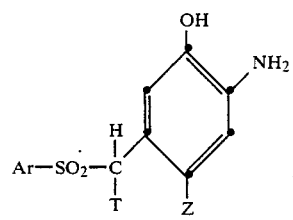

wherein Ar and T have the same significance as above and Z is a coupling-off group, as defined below.

Of the compounds mentioned above, it is preferred that T be selected from —COOH, —COOC₂H₅, phenyl, nitrophenyl, acetamidophenyl, carboxyphenyl,

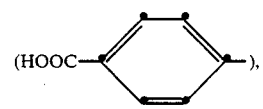

hydroxyphenyl, and alkoxyphenyl, wherein the alkoxy radical has up to about 30 carbon atoms.

In a highly preferred process embodiment, this invention comprises a method for preparing a compound having formula (A), (B), (C), or (D), said method comprising reacting in the presence of an acid promoter, (i) a 2-aminophenol or 3-aminophenol having the formula:

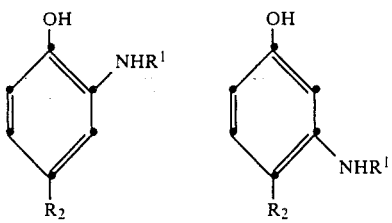

(ii) an unhindered non-enolizable aldehyde having the formula:

$R^5$—CHO, (III)

wherein $R^5$ is selected from the class consisting of —COOR and

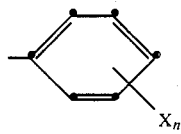

and (iii) a thiol (IV) or sulfinic acid (V) having the formulae:

$R^3$—SH   $R^3$—SO₂—H   (IV) (V)

In formulae (I)–(V) the various symbols have the same significance as above.

With regard to the aminophenol used as a reactant in the process of the invention, the parent compounds, 2-aminophenol and 3-aminophenol:

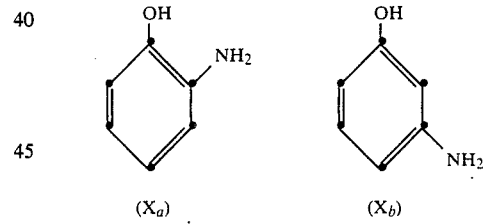

or a substituted derivative thereof, can be employed. In this reactant, substituents may appear on the benzene nucleus, or on the amino nitrogen. Preferably not more than one of the hydrogens bonded to the amino group is substituted. In other words, this invention is applicable to the use of primary and secondary amines.

When one of the amino hydrogens is replaced with another substituent, it is preferably replaced with a substituent (i) which does not interfere with the process of the invention to a significant extent, and (ii) is stable under the reaction conditions employed. In other words, preferred substituents do not react under the process conditions employed to give an untoward amount of unwanted product, nor do they retard the process by steric hindrance or other mechanism and thereby make the process inapplicable. Furthermore, preferred substituents do not decompose under the reaction conditions employed to give an untoward amount of decomposition product(s). For the purpose of this invention, substituents having these preferred characteristics are designated "inert substituents."

In formulae (I) and (II) $R^1$ is selected from the class consisting of hydrogen, and substituted or unsubstituted alkyl and aryl groups having up to about 30 carbon atoms. The substituted alkyl and aryl groups can have one or more "inert" substituents. Preferably $R^1$ is hydrogen or solely composed of carbon and hydrogen, i.e., a "hydrocarbyl" group. More preferably, it is hydrogen, phenyl, tolyl, or a lower alkyl radical, i.e., an alkyl radical having one to about four carbon atoms. Highly preferred alkyl radicals are primary and secondary lower alkyl radicals, i.e., radicals having up to about four carbon atoms. Most preferably the alkyl groups are straight chain, i.e., methyl, ethyl, n-propyl, n-butyl, and the like.

In the aminophenol reactants, it is preferred that the carbon atom which is para to the hydroxy group be unsubstituted; or in other words, that it be bonded to hydrogen. Thus, it is preferred that $R^2$ be hydrogen. When not hydrogen, it is preferred that it be a coupling off group, such as F, Cl, alkoxy, and aryloxy.

Coupling-off groups, defined by Z herein, are well known to those skilled in the photographic art. Such groups can determine the equivalency of the coupler, can modify the reactivity of the coupler, or can advantageously affect the layer in which the coupler is coated or other layers in the element by performing, after release from the coupler, such functions as development inhibition, bleach acceleration, color correction, development acceleration, and the like. Representative classes of coupling-off groups include halogen, particularly chlorine or fluorine, alkoxy, aryloxy, heterocyclyloxy, sulfonyloxy, acyloxy, carbonamido, imido, heterocyclic, thiocyano, alkylthio, arylthio, heterocyclylthio, sulfonamido, phosphonyloxy and arylazo. They are described in, for example, U.S. Pat. Nos. 2,355,169., 3,227,551., 3,432,521; 3,476,563; 3,617,291; 3,880,661; 4,052,212; and 4,134,766; and in U.K. patent Nos. and published application nos. 1,466,728; 1,531,927; 1,533,039; 2,006,755A; and 2,017,704A, the disclosures of which are incorporated herein by reference.

Examples of specific coupling off groups are as follows:

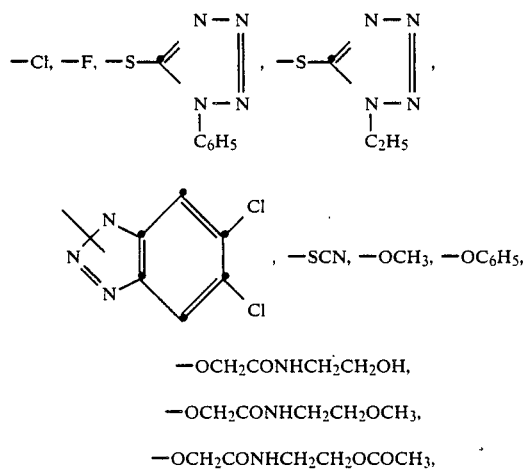

—OCH₂CONHCH₂CH₂OH,

—OCH₂CONHCH₂CH₂OCH₃,

—OCH₂CONHCH₂CH₂OCOCH₃,

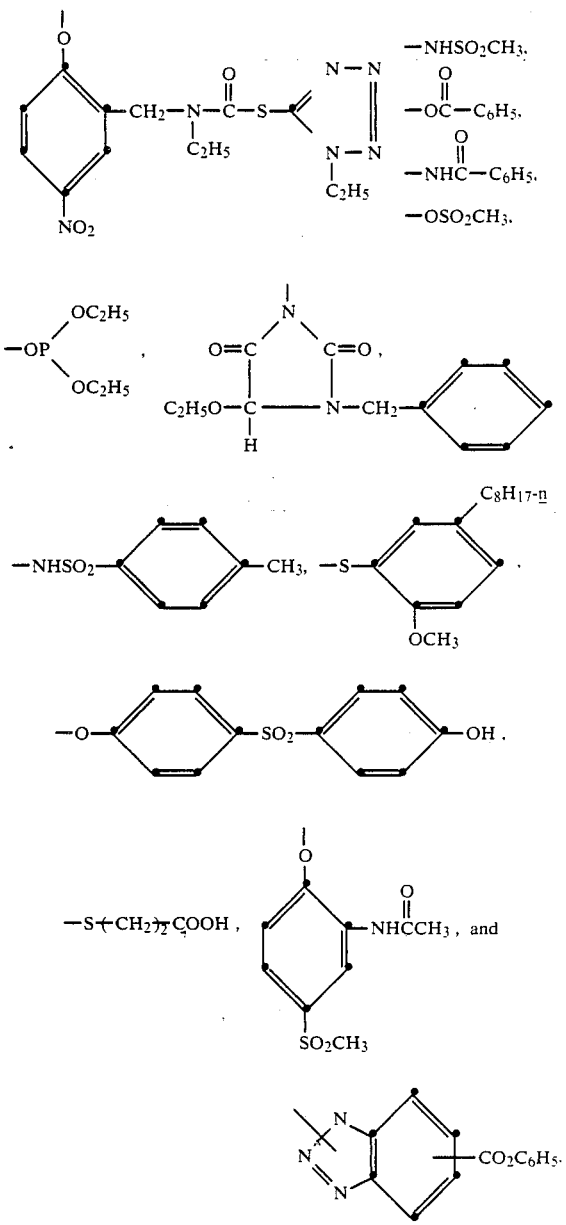

The coupling-off group as described can contain a water-solubilizing group, such as a carboxy group. The total hydrophilicity of the coupler and the dye formed from the coupler should not be high enough to cause the coupler and the dye formed to be mobile in the photographic element.

The aminophenol reactants may have "inert" substituents on the ring. Typical "inert" substituents are alkyl, alkoxy, halogen, carboxy ester, cyano, acetamino, and the like. Such substituents are exemplified by —CH₃, —C₁₀H₂₁, —C₁₄H₂₉, —OCH₃, —OC₁₀H₂₁, —OC₁₄H₂₉, —Cl, —F, $$-\underset{\underset{O}{\|}}{C}-OC_2H_5,$$

—CN, —NHCOCH₃, and the like.

It is to be understood that the aminophenol can be employed per se, or as an amine salt. Typical amine salts for use in this invention are salts of strong acids, such as amine hydrochlorides and amine sulfates. Such salts, and other amine salts in which the acid anion is inert or substantially inert in the process of this invention, can be employed. When the aminophenol is added as such a salt, it is not necessary to separately add an acid as a promoter.

The aldehyde used as a reactant in this invention is an aldehyde which (i) has at least two carbon atoms, and (ii) is unable to enolize. In other words, the aldehyde does not have a hydrogen bonded to a carbon atom alpha to the aldehydo group, and is, therefore, unable to form the enol structure

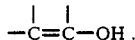

In addition to the above discussed characteristics, it appears that the aldehyde should not be too sterically hindered. In this regard, it has been noted that pivalyl aldehyde does not react when subjected to the process conditions used in this invention; see Comparative Example B below. Apparently, this aldehyde is too sterically hindered by the tertiary-butyl group therein to undergo the process. Therefore, it is recommended that compounds having such a structure adjacent to the aldehydo group not be employed in the process of this invention.

A preferred class of aldehydes for use in this invention has the formula $R^4OOC\text{---}CHO$, wherein $R^4$ is hydrogen or a substituted or unsubstituted alkyl or aryl group having up to about 30 carbon atoms. Such substituents have been discussed above.

Another preferred class of non-enolizable aldehyde that can be used in this invention is an aromatic aldehyde. The aromatic nucleus is preferably a carbocyclic aromatic nucleus such as the benzene ring or a benzene ring within a fused ring system. Although such aromatic aldehydes are preferred, it is to be understood that the aromatic nucleus can be derived from a heterocyclic ring compound which has aromatic characteristics. The aromatic nucleus may be substituted with other substituents besides the aldehydo group. Preferably, these substituents are inert substituents. Examples of inert substituents are mentioned above.

The thiol and sulfinic acid reactants used in this invention have the formula

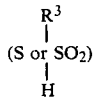

and can be any compound of this type that is a nucleophile under acidic reaction conditions. $R^3$ may be alkyl, aryl, or heterocyclic. Useful heterocyolic groups include, for example, tetrazoles, benzoxazoles, and benzothiazoles. The alkyl and aryl groups may be substituted or unsubstituted groups of having up to about 30 carbon atoms. Alkyl groups include methyl, ethyl, n-octyl, and n-decyl, and include substituted alkyl groups such as chloroethyl and hydroxypropyl. Useful aryl groups include phenyl, naphthyl, p-tolyl, p-dodecyloxypheny, and the like. Preferably, $R^3$ is aryl.

In those instances in which a sulfinic acid is used as a reactant, the acid need not be added per se. In other words, the sulfinic acid reactant can be added to the reaction mixture as the acid or as a salt thereof, e.g. an alkali metal salt such as a sodium or a potassium salt. When such a salt is employed, one uses sufficient acid promoter to transform the salt to the acid. This amount of acid promoter is in addition to that required to react with the aminophenol. Use of the promoter for this purpose is exemplified below.

Generally speaking, the reactants are employed in stoichiometric or substantially stoichiometric amounts. Higher yields are obtained when a slight excess (up to about 0.5 mole) of the aminophenol are used in the reaction.

The process is conducted in the presence of an acid promoter. For this purpose, a strong mineral acid such as hydrochloric acid, hydrobromic acid, sulfuric acid, or the like, is preferred. Thus, any acid which is sufficiently strong enough to react with the aminophenol to form the amine salt can be employed.

The amount of the promoter should at least be equal, in moles, to the number of moles of aminophenol added to the reaction mixture. An excess of promoter can be used if desired. There is no real upper limit on the amount of promoter, this being defined by such secondary considerations as economics, ease of recovery of product, size of the reaction vessel, etc.

The described reaction is carried out in a solvent for the reactants, preferably in a polar solvent in which the aniline salt is soluble. Examples of useful solvents are methanol, ethanol, and the like, acetonitrile and dimethylformamide (DMF), and acids such as acetic acid, and the like. Any polar solvent which does not react in a deleterious way with one or more of the reactants under the reaction conditions employed, can be used in the process of this invention. For purposes of description of the invention, such solvents are referred to as "inert polar solvents." Solvent quantities of such a reaction medium are employed. In other words, one uses enough solvent to dissolve all or substantially all of the reactants, and to provide good mixing. There is no real upper limit on the amount of solvent used, this being defined by such secondary considerations as referred to above.

A solvent need not be used if the reactants can be suitably contacted without one. Thus, use of a solvent is a preferred but not a critical process expedient.

The process of this invention is conducted at a mildly elevated temperature to facilitate the reaction. In general, one uses a reaction temperature sufficient to give a reasonable reaction rate, but below that temperature which causes decomposition of product or reactants. Thus, an applicable reaction temperature is generally in the range of from about 50° to about 100° C. However, it is to be understood that the process of this invention is not critically dependent on any reaction temperature. Thus, the process temperature is an important, but not a critical reaction expedient.

The process proceeds well at ambient pressures, and such pressures are preferred.

The time of reaction is not a truly independent variable, but is dependent at least to some extent on the inherent reactivity of the reactants, the process temperature, and similar considerations. In general, higher process temperatures can be used with shorter reaction times. At the temperatures within the ranges discussed above, the reaction times are usually in the range of from about 30 minutes to 3 hours. Reaction times somewhat outside this range can be employed.

EXAMPLE 1

A mixture of 18.0 g (0.1 mol) of 5-chloro-2-hydroxyaniline hydrochloride, 9.2 g (0.1 mol) of glyoxylic acid monohydrate and 12.4 g (0.1 mol) of p-toluenethiol in 150 ml glacial acidic acid and 15 ml water was refluxed for 2 hours with stirring. After cooling to room temperature the reaction mixture was poured into an aqueous solution of sodium acetate. The solid which precipitated out was collected, washed with water and then with ligroin. Recrystallization from methanol gave 28.0 g (86.6%) of white crystalline solid; m.p. 205–206° C. (dec.). The structure of the product:

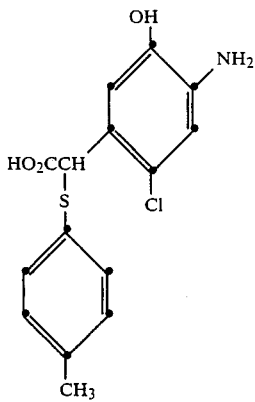

is consistent with its H-NMR spectrum.

Calculated for $C_{15}H_{14}ClNO_3S$: C,55.64; H,4.36; N,4.33; S,9.90

Found: C,55.47; H,4.36; N,4.38; S,9.79 The above example illustrates several useful embodiments including:

(a) the use of a salt of the aminophenol as a reactant,
(b) the use of an aliphatic non-enolizable aldehyde as a reactant,
(c) the use of an arylthiol as a reactant, and
(d) the use of an aqueous organic acid as a liquid reaction medium.

The process of the above example also illustrates the use of an aminophenol as a reactant which has an inert substituent in the position para to the hydroxy group. As discussed above, other inert substituents can appear in that (and other positions about the ring). Preferred inert substituents in the afore-mentioned para position are alkoxy and aryloxy, such as methoxy, phenoxy, and similar ether groups having up to about 30 carbon atoms.

The product and process of the above example illustrate the preparation of a "functional" product. As can be seen by the product structure, there is a reactive, i.e. functional group (specifically the carboxy group) introduced by a reactant employed in the process. This reactive group can be utilized to form other molecules by subsequent chemical reaction. To prepare a "functionalizable" compound using the process of the above example, one may substitute for the glyoxalic acid, a derivative thereof wherein the carboxy group is esterified. As recognized by a skilled practitioner, the "functionalizable" ester group which would be introduced into the product (and which is comparatively non-reactive) can be transformed into a "functional" group by hydrolysis to produce the non-esterified (reactive) carboxy radical.

EXAMPLE 2

To a solution of 10.9 g (0.1 mol) of 2-aminophenol in 150 ml ethanol was added with stirring 17.4 ml (0.2 mol) of conc. hydrochloric acid, 10.6 g (0.1 mol) of benzaldehyde and a solution of 16.4 g (0.1 mol) of sodium benzenesulfinate in 25 ml water. The mixture was heated on a steam bath and refluxed for 1 hr. After cooling to room temperature, the mixture was poured into ice water and carefully neutralized with a 10% solution of sodium bicarbonate. The solid was collected and washed with water. Recrystallization from ethanol gave 30 g (88.5%) of white crystalline solid; m.p. 196–198° C. The structure of the compound is consistent with its H-NMR spectrum.

Calculated for $C_{19}H_{17}NO_3S$: C,67.24; H,5.05; N,4.13

Found: C,67.37; H,5.11; N,4 10 The product was assigned the formula:

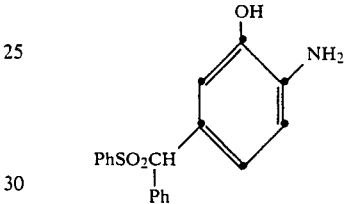

This example illustrates several preferred embodiments of this invention including:

(a) use of a free aminophenol (rather than a salt thereof),
(b) use of an aromatic aldehyde,
(c) use of a salt of a sulfinic acid, and
(d) use of an acid promoter in an amount to combine with the aminophenol to form a salt and to produce the sulfinic acid from its salt.

EXAMPLE 3

To a mixture of 9.1 g (0.05 mol) of 2-amino-4-chlorophenol hydrochloride and 4.6 g (0.05 mol) of glyoxylic acid monohydrate in 150 ml ethanol was added with stirring 7.8 g (0.05 mol) of p-toluenesulfinic acid. The mixture was stirred at room temperature for 15 minutes then heated on a steam bath and refluxed for 1.0 hour. After cooling to room temperature, the mixture was poured into ice water. The gum which separated was collected, washed with 10% $NaHCO_3$ solution and several times with water and air dried. Upon trituration with ethyl acetate a solid was formed. Thin layer chromatography showed the solid to be essentially pure. Yield was 14.6 g, 82% m.p. 189–190° C. dec. The structure of the compound:

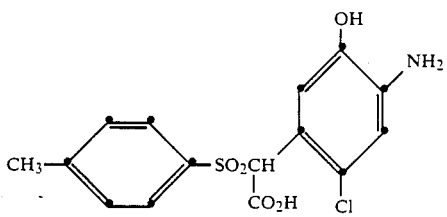

is consistent with its H-NMR spectrum.

Calculated for $C_{15}H_{14}ClNO_5S$: C,50.64; H,3.97; Cl,9.96; N,3.94

Found: C,50.57; H,3.79; Cl,10.01; N,3.94 Typical compounds of this invention include those having the formula:

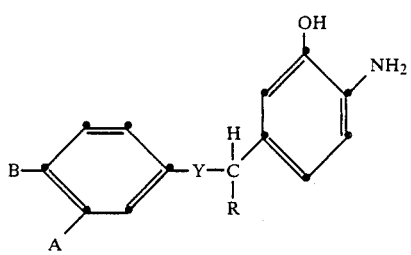

and are illustrated by compounds in the following table.

| | COMPOUNDS OF FORMULA E | | | |
|---|---|---|---|---|
| Compound | A | B | Y | R |
| 1 | —H | —H | —S— | —$CO_2H$ |
| 2 | —H | —H | —$SO_2$— | —$CO_2H$ |
| 3 | —H | —H | —$SO_2$— | —$CO_2C_2H_5$ |
| 4 | —$C_{12}H_{25}$ | —H | —$SO_2$— | —$CO_2H$ |
| 5 | —H | —$NHSO_2CH_3$ | —$SO_2$— | —$CO_2H$ |
| 6 | —H | —H | —$SO_2$— | —$C_2H_5$ |
| 7 | —$OC_{12}H_{25}$ | —H | —$SO_2$— | —$C_6H_5$ |
| 8 | —H | —H | —$SO_2$— | p-$NO_2$—$C_6H_5$— |
| 9 | —H | —H | —$SO_2$— | p-$C_{12}H_{25}O$—$C_6H_5$— |

The compounds of the above table, and the compounds produced in the process of the above examples, are illustrative but non-limiting examples of the compounds of this invention. The compounds of the table can be made by the method of this invention by modifying the procedure of the examples as required, e.g., by substitution of the obvious starting materials for those used in the processes of the examples. It is to be understood that compounds similar to the above illustrative compounds can be made by substituting the appropriate 3-aminophenol for the 2-aminophenol used to prepare the illustrative compounds.

The compounds of this invention are useful for preparing biologically active materials such as antifungal and antibacterial agents. They also can be used for preparing insecticides and plant growth regulating agents, e.g. herbicides. They are useful for the formation of dye and dye intermediates. They can also be employed for the preparation of photographically useful compounds such as dyes, stabilizing agents, image couplers, image modifiers such as development inhibitor releasing couplers, bleach accelerator releasing couplers, and colored masking couplers.

The following comparative examples demonstrate that seemingly related reactants fail to react, or give a product with an entirely different structure, and thereby illustrate the surprising nature of the process of this invention, and the products produced thereby.

COMPARATIVE EXAMPLE A

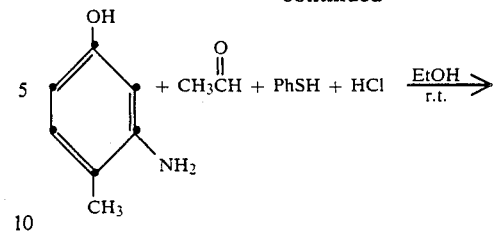

-continued

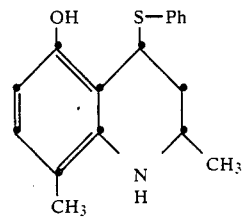

Procedure:

To a solution of 12.3 g (0.1 mol) of 3-amino-5-methyl phenol in 150 ml ethanol was added with stirring 8.6 g (0.1 mol) of conc. hydrochloric acid, 13.2 g (0.3 mol) of acetaldehyde and 11.0 g (0.1 mol) of benzenethiol. The mixture was stirred at room temp. for 2 hours, then poured into water and carefully neutralized with a 10% solution of sodium bicarbonate. The precipitated solid was collected, washed with water and then with isopropyl ether. Thin layer chromatography showed the product to be pure. Yield was 20.8 g (73%), m.p. 132–135° C. The structure of the compound is consistent with its H-NMR spectrum.

Calcd. for $C_{17}H_{19}NOS$: C,71.54; H,6.71; N,4.91

Found: C,71.70; H,6.91; N,4.81

COMPARATIVE EXAMPLE B

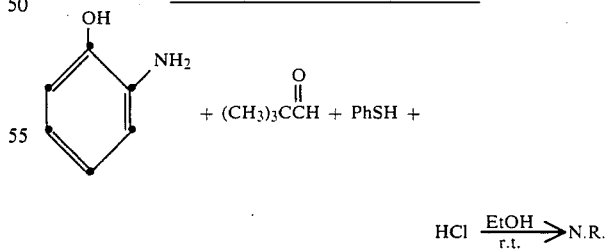

to a mixture of 10.4 g (0.1 mol) of 2-aminophenol and 8.6 ml (0.1 mol) of conc. HCl in 150 ml ethanol was added with stirring 8.6 g (0.1 mol) of pivalyl aldehyde and 11.0 g (0.1 mol) of benzenethiol. The mixture was refluxed on a steam bath for 3 hours. Thin layer chromatography showed no reaction product being formed with all the starting materials remaining unreacted. Longer reflux time did not appear to have an effect.

The invention has been described in detail above with particular reference to preferred embodiments thereof. A skilled practitioner familiar with the above detailed description can make many modifications and substitutions thereof without departing from the scope and spirit of the following claims.

We claim:

1. An aminophenol wherein the amino group and the hydroxy group are either ortho or meta to one another, and wherein the amino group has at least one hydrogen bonded to the amino nitrogen, and the third valence of said nitrogen is satisfied by bonding to hydrogen or an alkyl or aryl group having up to about 30 carbon atoms, and wherein the position para to said hydroxy group is unsubstituted or substituted with a coupling off group selected from the group consisting of —Cl, —F, —OCH₃, —OC₆H₅, —OCH₂CONHCH₂CH₂OH, —OCH₂CONHCH₂CH₂OCH₃, —OCH₂CONHCH₂CH₂OCOCH₃,

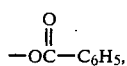

—NHSO₂CH₃,

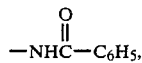

—OSO₂CH₃,

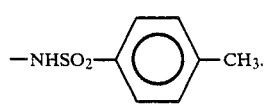

—S(CH₂)₂COOH,

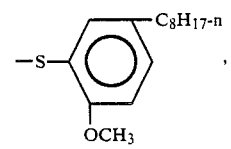

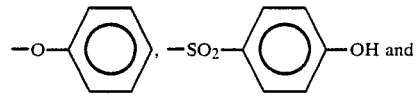

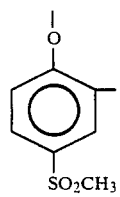

, and the position para to the amino group is bonded to a carbon atom that is in turn bonded to (i) a hydrogen atom, (ii) a substituent selected from the class consisting of alkylthio, arylthio, alkylsufonyl, and arylsulfonyl groups wherein the alkyl and aryl groups have up to about 30 carbon atoms, and (iii) a group selected from carboxy and carboxy ester represented by COOR, wherein R is an alkyl or aryl radical having up to about 30 carbon atoms.

2. A compound of claim 1 having the formula

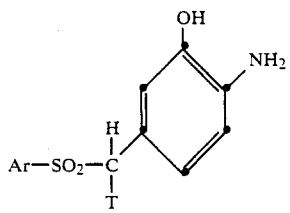

or the formula

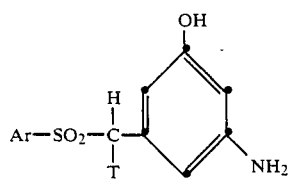

wherein Ar is an aryl group having up to about 30 carbon atoms, and T is selected from the class consisting of carboxy and, carboxy ester represented by COOR, R having up to about 30 carbon atoms.

3. A compound of claim 1 having the formula:

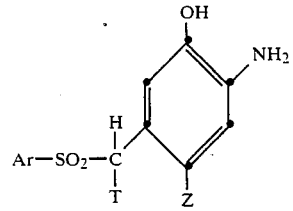

or the formula:

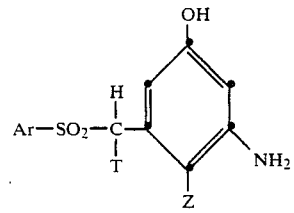

wherein AR is an aryl group having up to about 30 carbon atoms, and T is selected from the class consisting of carboxy and, carboxy ester represented by COOR, R having up to about 30 carbon atoms and Z is a coupling off group.

4. A compound of claim 3 wherein T is selected from —COOH, —COOC₂H₅, and p-carboxyphenyl.

* * * * *